United States Patent [19]
Moffett

[11] Patent Number: 5,891,069
[45] Date of Patent: Apr. 6, 1999

[54] CERVICAL EXTRACTION COLLAR AND METHOD OF IMMOBILIZING A CERVICAL INJURY

[76] Inventor: Lynn Moffett, 251 Greenwood Ave., Bethel, Conn. 06801

[21] Appl. No.: 6,425

[22] Filed: Jan. 13, 1998

[51] Int. Cl.⁶ .................................................. A61F 5/00
[52] U.S. Cl. .............................................. 602/18; 602/13
[58] Field of Search .................................. 602/17–19, 13, 602/6; 128/845, 857, 870, DIG. 23; 2/44, 45

[56] References Cited

U.S. PATENT DOCUMENTS

| | | | |
|---|---|---|---|
| 3,745,998 | 7/1973 | Rose | 602/13 X |
| 3,762,404 | 10/1973 | Sakita | 602/6 |
| 4,657,003 | 4/1987 | Wirtz | 602/13 X |
| 4,757,554 | 7/1988 | Blair | 602/18 X |
| 4,881,529 | 11/1989 | Santos | 602/18 |
| 4,885,811 | 12/1989 | Hayes | 602/13 X |
| 5,603,690 | 2/1997 | Barry | 602/13 X |
| 5,618,263 | 4/1997 | Alivizatos | 602/6 |

*Primary Examiner*—Linda C.M. Dvorak
*Attorney, Agent, or Firm*—A. Jose Cortina; R. Todd Morgan; Kilpatrick Stockton LLP

[57] ABSTRACT

A cervical extraction collar is constructed so that it does not require taking off of a helmet in the event of a sports injury on the field. A main portion of the collar serves to lock a helmet and shoulder pads together, such as the helmet and shoulder pads of a football player or hockey player. A substance is contained within the main portion of the collar to rigidify the collar, and can be initially drawn away from the main portion into tails extending from the collar. After the main portion is placed between the back of the helmet and the shoulder pads, the substance in the tails can then be reinserted into the main portion to expand and brace the main portion against the back of the helmet on one side, and against the shoulder pads of the player on the other side, thereby providing a cervical support without requiring removal of the helmet to attend to the injury. The materials making up the collar are preferably all transparent to x-rays.

22 Claims, 2 Drawing Sheets

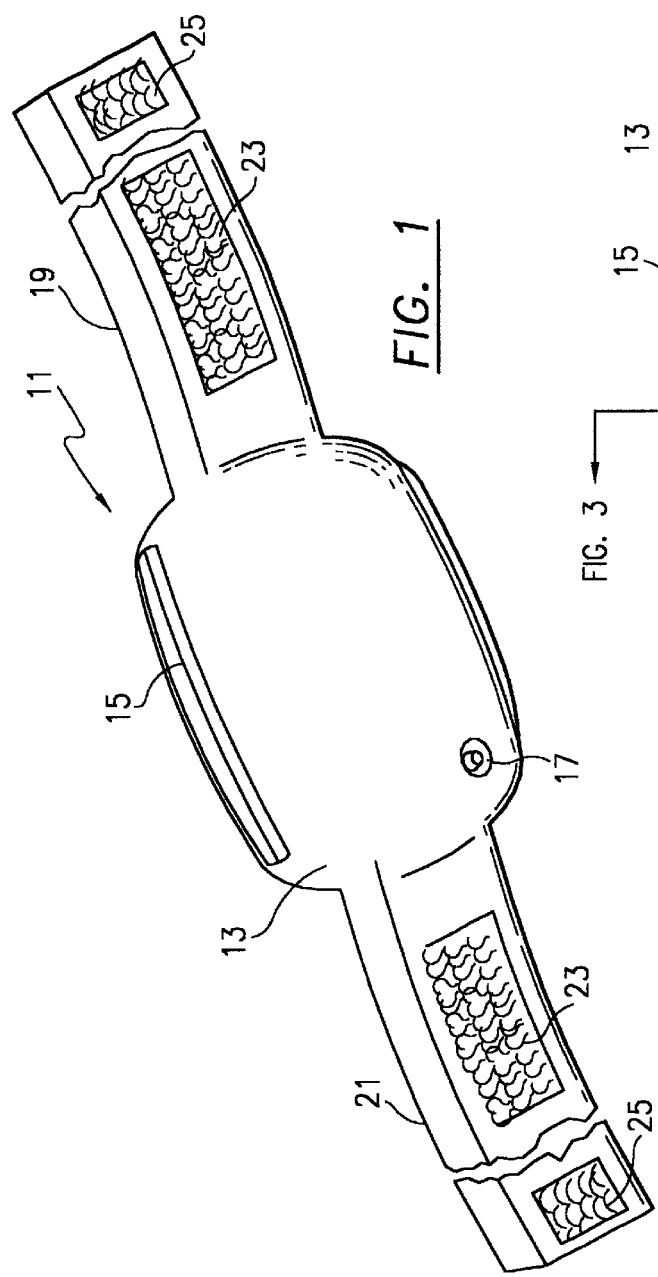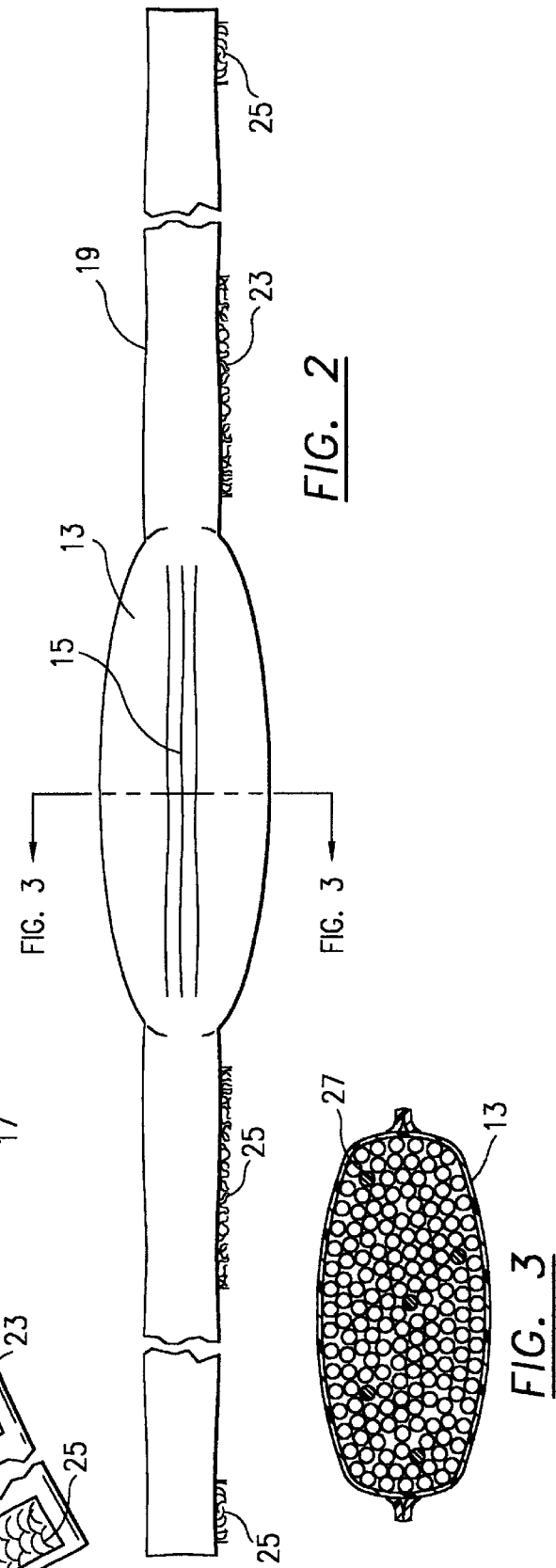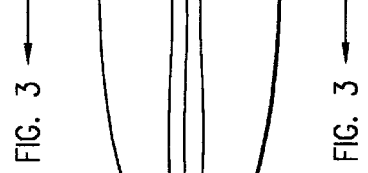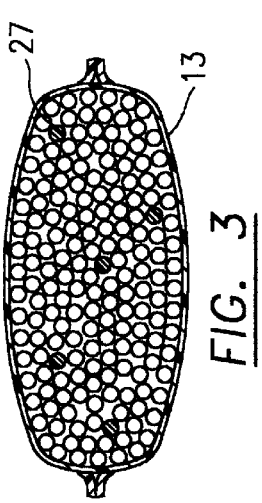

CERVICAL EXTRACTION COLLAR AND METHOD OF IMMOBILIZING A CERVICAL INJURY

BACKGROUND OF THE INVENTION

The present invention relates to cervical spinal immobilization device and, more particularly, to a device particularly adapted for use with participants in contact sports wearing impact protective helmets for protecting the head and skull area from impact injuries, and wearing other padding such as shoulder pads.

It has long been known in contact sports, especially football, that impacts are dangerous to the participants. Thus, it has been common to provide various protective equipments for football players and the like, including padding, and especially including impact protective helmets to protect the head and skull area from impact injuries. In addition, due to the often traumatic body collisions occurring in such sports, it has also been common to provide additional protective equipments such as padding for the shoulder area extending around and behind the neck in close proximity to the helmets which are used. This is typical, for example, in football, hockey, lacrosse and the like sports.

While such helmets and shoulder pads have been significant in reducing direct impact injuries from blows to the head, the current style of rigid helmet with face guard has introduced an increased risk of paralyzing injury. This is because the rigid helmet and rigid face guard, combined with the shoulder pads, are braced to prevent direct impact injury to the face area and head, and result in the transfer of all forces to the head as a body. The head and skull being encased within a padded helmet is securely gripped by the helmet and any force applied to the helmet moves the entire head and is concentrated in the cervical region of the spine. This has resulted in an increasing incidence of broken necks and cervical region injuries.

In treating such an injury it becomes important to support and stabilize the cervical region in order to reduce the severity of the injury and minimize the danger of paralysis. Moreover, because of such frequent injury, new standards have been established, in the emergency medical care field, for the proper handling of trauma patients in order to improve the patient's chances for recovery. Such proper handling requires immediate attention to the patient in the injury situation, and thereafter, immediate transport to a medical facility for treatment. Immediate treatment includes completely immobilizing the injury before movement, and stabilizing and holding the injured area in an immobilized manner during transport to the medical facility for treatment.

Several cervical and spinal immobilization devices have been developed. Generally these devices comprise short or long spine boards which are used in association with other devices such as cervical collars, body harnesses or straps. One example of a prior art cervical collar is an inflatable neck and head support for use by wearer. This prior art device is a generally rectangular body of flexible gas impervious material with two side panels that is sealed around its entire periphery to form a closed chamber. A valve is mounted in the body to inflate and deflate the chamber. Fasteners are mounted on spaced portions of the body to allow, upon inflation of the chamber, the forming of an annular shape and retaining the annular shape. A modification of this support includes a thin layer of closed cell foam adhered to a wall of the closed chamber to provide a degree of rigidity to the head support.

A more complex device of the prior art is a cervical support for use in immobilizing victims of spinal injuries. The cervical support includes a cervical splint dimensioned to extend from the top of the head to about mid-back of an adult victim, and is shaped to follow the outline of the victim's head and shoulders. The support includes head and chest straps for securing the victim to the splint. The head straps wrap about the forehead and the chin of the victim, and the chest straps extend over the shoulder and under the opposite arm in criss-cross fashion across the chest.

Another more complex type prior art device is a cervical spine immobilization device made up of a corrugated plastic board member. The device includes a reinforcement panel at a critical central zone. Various portions of the device are held together in their secured locations by straps and belts such as those made of nylon webbing attached to the device.

In the area of sports injuries, particularly where the injured person is wearing a sports helmet, one prior art device, which is used to attempt to prevent injury, provides for a flexible support brace which transfers excessive back motion of a sports helmet through a flexible interlinked brace. The brace floats freely between two spaced circumferential spans on the helmet during normal play, but engages with the helmet and collapses to a braced configuration if the helmet is excessively pulled back or pushed forward. In the braced configuration, helmet loads are transferred to the shoulder pads of the player directly, thus transferring excessive head loads into the chest area of the player where they can be more safely absorbed. This device, while taking advantage of the use of the helmet as part of the support structure, is not used to immobilize the cervical region of a person that has been injured, but is instead used to attempt to avoid injuries by transferring the forces applied to the helmet in the event of impact.

In accordance with the device and method of the invention, the complications of the prior art are avoided and a simple device is provided which serves to immobilize a cervical region of a person who has been injured, while wearing a helmet and shoulder pads, without the necessity of removing the helmet, or require any movement of the injured person prior to complete immobilization, which would risk additional injury to the cervical region.

SUMMARY OF THE INVENTION

In accordance with the invention, in one aspect there is provided a cervical extraction collar for immobilizing the injured cervical region of a person. The collar includes a main body for containing a substance therein for rigidifying the main body, and for immobilizing a helmet of a person when the main body is placed between the back lower edge of the helmet of the person and shoulder pads worn by the person. Tail portions extend from the main body to allow the substance to be initially withdrawn from the main body to allow manipulation of the main body. This allows placement of the main body between the helmet and the shoulder pads worn by the person, and thereafter, once the main body is placed in position, the tails are used to move the substance back into the main body portion to rigidify the main body portion, and to thereby immobilize the cervical region of the person by immobilizing the helmet relative to the shoulder pad. The collar can be installed by simply passing the collar through the gap formed between an injured person's neck and the ground. Thus, no movement of the person is required prior to complete immobilization.

Preferably, the substance is made up of beads in an amount to substantially completely fill the main body portion. The main body portion also preferably includes a channel on the upper surface thereof for receiving the back lower edge of the helmet securely therein. The amount of beads in the collar is such as to substantially completely fill the main body when all of the beads are located in the main body, and an air valve is provided to allow air to be removed from the main body as the cervical collar is secured between a helmet and shoulder pads to further rigidify the main body.

In another aspect of the invention, there is provided a method of immobilizing a cervical region of a person wearing a helmet. The method involves securing the cervical collar of the invention by engagement with the lower edge of a helmet being worn by a person and the upper surface of shoulder pads being worn by the person. Initially, the substance, e.g. beads, in the main body portion is moved into the tails. The main body portion is then wedged between the helmet and the shoulder pads, and the substance, i.e., beads, reintroduced into the main portion.

In a preferred embodiment air can then be withdrawn through a valve, preferably located on the main body. The tails can be attached to the face cage of the helmet, if one is present, further assisting in the immobilization. As the collar is preferably made of all x-ray penetrable material, the injured person may remain immobilized until a diagnosis of cervical fracture or dislocation is determined.

BRIEF DESCRIPTION OF THE DRAWINGS

Having briefly described the invention, the same will become better understood from the following drawings taken in conjunction with the detailed description, in which:

FIG. 1 is a perspective view of the cervical collar in accordance with the invention showing the main body, tails with bristle hook and loop material, a channel for receiving the lower back edge of a helmet, and an air valve;

FIG. 2 is a top view of the cervical collar in accordance with the invention;

FIG. 3 is a cross sectional view of the cervical collar of the invention taken along lines FIG. 3 of FIG. 2.

DETAILED DISCUSSION OF THE INVENTION

Figure 4:
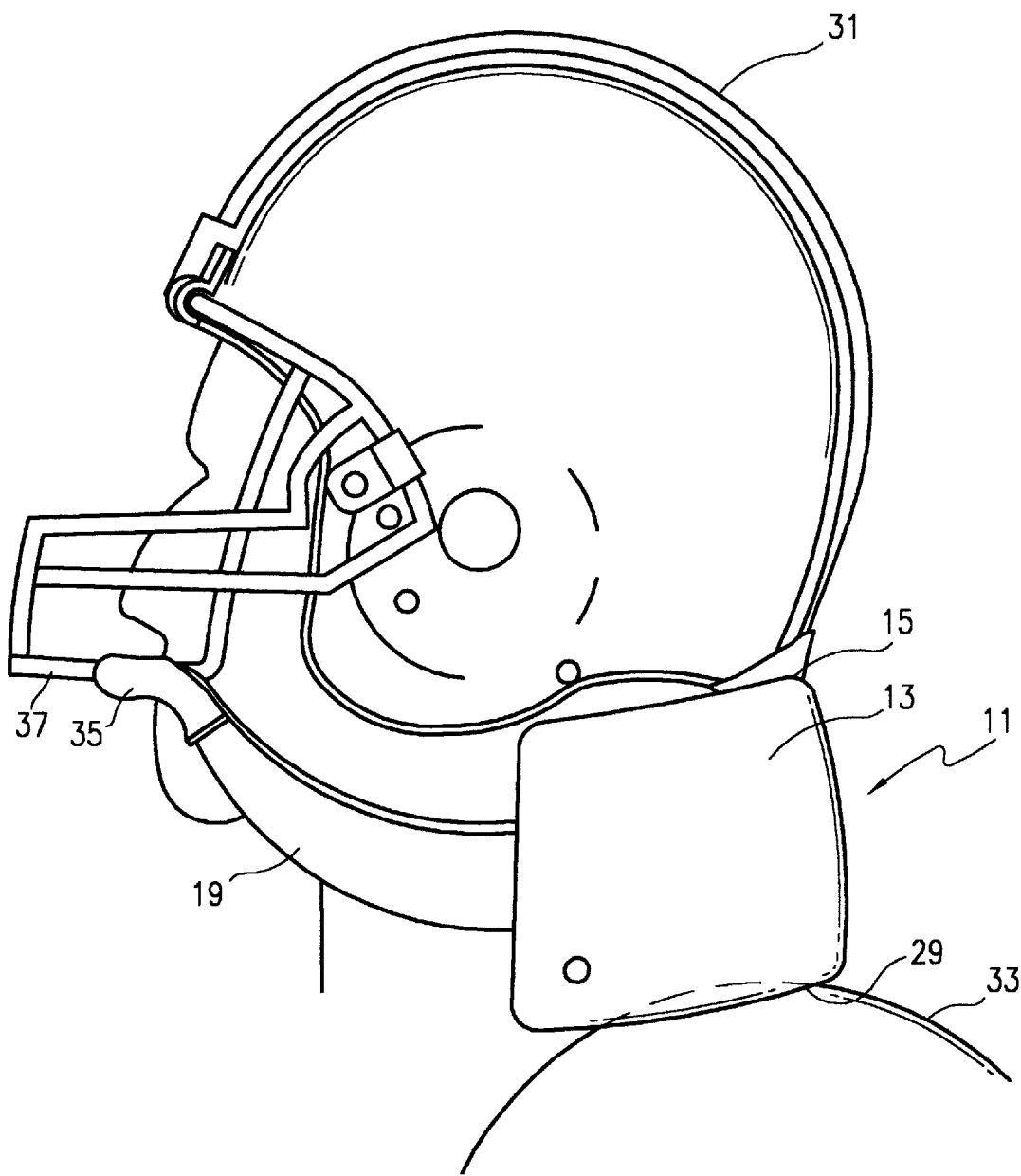
FIG. 4 is a side view of the cervical collar in accordance with the invention, in place on a person supporting the cervical region between a helmet and the shoulder pads of the person.

Referring to the drawings, wherein like reference numbers designate like or corresponding parts throughout the several views, there is shown in FIG. 1 a cervical collar 11 in accordance with the invention. Cervical collar 11 includes a main body portion 13 preferably having a groove 15 and tail portions 19 and 21 with bristle hook and loop material strips 23 and 25. Such bristle hook and loop material strips can be, for example, VELCRO® material such as is readily commercially available for fastening purposes. An air valve 17 serves for withdrawing substantially all air from the cervical collar 11, which is made at its main body portion 13 and tails 19 and 21 of flexible material and hollow construction so that both the tails 19 and 21 and the main body portion 13 can be filled with a moveable substance which serves, when filled into the main body portion 13, to rigidify the main body portion 13 in a manner to provide support as will be explained hereinafter.

More specifically, as shown in FIG. 2, and along broken cross line FIG. 3 of FIG. 2, in FIG. 3, the main body portion 13 is shown as containing a substance 27 therein. Preferably, the substance is made up of beads, typically, polyurethane beads which when contained in the main body portion 13 substantially completely fill the main body portion 13 and as air is extracted through air valve 17, serves to provide a substantially rigid main body portion 13.

The beads 27 can be, for example, polyurethane beads or any other like material, which when air is extracted from the collar, becomes rigid as a compact mass. More specifically, the beads may be of the type used, for example, by Cramer, Inc. in their rigid form vacuum immobilizers described in the Micromedics catelog for 1997. These beads are conventional and well known to those of ordinary skill in the art. Of course, as may be appreciated, the invention is not limited to the use of the Cramer Inc. beads, and other like substances may be used, provided they result in a sufficiently rigid compact mass to provide sufficient immobilization.

FIG. 4 shows the cervical collar 11 in accordance with the invention shown in use for immobilizing the cervical region of a user who has been injured.

In its simplest mode of use, when a person has been injured on the field of play, for example, playing football, instead of having to remove the helmet 31 and shoulder pads 33, which can result in a risk of greater injury, the substance 27, i.e., beads, from the main body portion 13 of the cervical collar 11, are moved from the main body portion 13 into the tails 19 and 21. This allows some flexibility and the ability to manipulate the main body portion 13 into position between the lower back edge of a helmet 31 and the shoulder pads 33 of a person or player who has been injured in the cervical region. The lower back portion of the helmet 31 is received preferably within groove or channel 15 and the bottom 29 of the main body portion 13 abuts against shoulder pads 33 such as to be snugly received between the bottom of the helmet 31 and the shoulder pads 33. Thereafter, the beads, or other substance 27, are moved back into the main body portion 13 to rigidify the main body portion 13. As a way of further eliminating any movement of the main body portion 13, air can be extracted through air valve 17.

As may be appreciated, the cervical collar 11 can be made of many flexible materials, for example, fabric or plastic material. Preferably, all the materials for the collar are x-ray penetrable to allow the injured person to remain immobilized until a diagnosis or cervical fracture or dislocation is determined.

In the event of an injury to a player wearing a helmet with a face cage 37, the tails 19 and 21 can be further more advantageously be used, once the substance 27 from the main body portion 13 is removed therefrom and reintroduced into the main body portion 13, by looping the tail 19, 21 end portions around a portion of the face cage 37 at an end 35 of the tail portions 19 and 21 to secure the tails 19 and 21 by engagement of the corresponding VELCRO® material portions 23 and 25.

As also may be appreciated, due to compaction when air is removed, the substance 27 will not move back into the tail portions 19 and 21. Thus, no back valves are required in the tail portions 19 and 21.

While certain representative embodiments and details have been shown and described for the purpose of illustrating the invention, it will be apparent to those skilled in the art that various changes and modifications other than those referred to may be made therein without departing from the spirit or scope of the invention.

What is claimed is:

1. A cervical extraction collar for immobilizing an injured cervical region of a person wearing at least a helmet and shoulder pads, comprising;

a main body portion having a main body portion cavity therein, said main body portion further comprising a channel disposed on a surface of said main body portion for receiving the lower rear edge of a helmet worn by a person;

a substance contained within said main body portion cavity for rigidifying said main body portion, and for immobilizing the helmet worn by a person by being placed between the back lower edge of the helmet and the shoulder pads worn by the person; and tail portions extending from said main body portion defining tail portion cavities which are interconnected with said main body portion cavity for allowing said substance to be withdrawn from said main body portion for allowing placement of said main body portion between the helmet and the shoulder pads worn by a person, and for allowing said substance to be moved back into said main body portion to rigidify the main body to thereby immobilize the cervical region of a person by maintaining the helmet in a fixed position relative to the shoulder pads.

2. A cervical extraction collar as in claim 1 wherein said main body portion and tail portions are made of flexible material, and wherein said substance comprises beads in an amount to substantially completely fill said main body portion.

3. A cervical extraction collar as in claim 1 wherein said tail portions are configured to be secured to a face cage of a helmet worn by a person.

4. A cervical extraction collar as in claim 3 wherein said tail portions further comprise complimentary bristle hook and loop material strips at the ends thereof to allow the tail portions to be secured to said face cage by wrapping each one of said tail portions around at least one bar of said face cage, to secure the complementary material strips to each other, thereby securing the tail portions to the face cage.

5. A cervical extraction collar as in claim 1 wherein said substance comprises plastic beads.

6. A cervical extraction collar as in claim 1 wherein said main body portion and said tail portions are made of fabric, and said collar is transparent to x-rays.

7. A cervical extraction collar as in claim 1 wherein said main body portion and said tail portions are made of plastic material.

8. A cervical extraction collar as in claim 1 further comprising an air valve for removing air from said cervical collar for increasing the rigidity of the cervical collar.

9. A cervical collar for immobilizing an injured cervical region of a person wearing at least a helmet, comprising;

a main body portion having a main body portion cavity therein, said main body portion being of sufficient size to fit in contact between the shoulder region and the helmet of a person;

tail portions extending from said main body portion defining tail portion cavities which are interconnected with said main body portion cavity;

a substance disposed within said main body portion cavity and said tail portion cavities capable of being moved between said tail portions and said main body portion, wherein said main body portion is maintained in an essentially rigid shape when said substance is moved from said tail portions into said main body portion; and a channel disposed in a surface of said main body portion to receive the rear lower edge of a helmet so as to keep the helmet in an immobilized position.

10. A cervical collar as in claim 9 wherein said substance comprises beads in an amount necessary to substantially completely fill said main body portion.

11. A cervical collar as in claims 9 or 10 further comprising an air valve for removing air from said cavity for further rigidifying said cervical collar.

12. A cervical collar as in claim 11 further comprising means for securing said tail portions to a face cage of a helmet.

13. A cervical collar as in claim 12 wherein said means for securing said tail portions to a face cage of a helmet comprises wrapping said tail portions around at least one bar of a face cage of a helmet, then securing the ends of said tail portions by use of bristle hook and loop material strips disposed on the end of said tail portions.

14. A method of immobilizing a cervical region of a person wearing a helmet, comprising the steps of:

placing a cervical extraction collar beneath the cervical region of a person so that it is disposed between the helmet and shoulder area of the person;

securing said cervical collar by engaging the rear lower edge of the helmet in a channel disposed in the upper surface of said cervical collar for receiving the rear lower edge of the helmet, and by placing the lower surface of said cervical collar in contact with the shoulder region of the person; and forcing a substance into a cavity defined within the main body portion of said cervical collar from adjoining cavities defined within tail portions connected to the main body portion in order to make the main body portion substantially rigid thereby substantially immobilizing the cervical area.

15. A method of immobilizing a cervical region as in claim 14 further comprising the step of securing said tail portions to a face cage attached to the helmet worn by a person.

16. A method of immobilizing a cervical region as in claim 15 wherein said tail portions further comprise complimentary bristle hook and loop material strips at the ends thereof, and wherein the step of securing said tail portions to a face cage attached to the helmet worn by a person further comprises doubling each one of said tail portions around a bar of said face cage and securing one strip of material of each one of said tail portions to its complimentary strip of material.

17. A method of immobilizing a cervical region as in claim 16 wherein said cervical collar has an air valve, and further comprising comprising the step of withdrawing substantially all the air from said cervical collar after the cervical collar has been placed beneath the cervical region of a person and after said substance has been reintroduced into said main body portion.

18. A method of immobilizing a cervical region as in claim 15 wherein said cervical collar has an air valve, and further comprising comprising the step of withdrawing substantially all the air from said cervical collar after the cervical collar has been placed beneath the cervical region of a person and after said substance has been reintroduced into said main body portion.

19. A method of immobilizing a cervical region as in claim 14 wherein said cervical collar has an air valve, and further comprising comprising the step of withdrawing substantially all the air from said cervical collar after the cervical collar has been placed beneath the cervical region of a person and after said substance has been reintroduced into said main body portion.

20. A method of immobilizing a cervical region as in claim 14 wherein said substance comprises plastic beads in an amount to substantially completely fill said main body portion, and wherein said main body portion and said tail portions are made of flexible material.

21. A method of immobilizing a cervical region as in claim 14 wherein said main body portion and said tail portions are made of fabric, and said collar is transparent to x-rays.

22. A method of immobilizing a cervical region as in claim 14 wherein said main body portion and said tail portions are made of plastic material.

* * * * *